(12) United States Patent
Xu et al.

(10) Patent No.: US 10,653,388 B2
(45) Date of Patent: May 19, 2020

(54) DEVICE AND METHOD FOR AUTOMATIC PNEUMOTHORAX DETECTION

(71) Applicant: KONINKLIJKE PHILIPS N.V., Eindhoven (NL)

(72) Inventors: Jingping Xu, Eindhoven (NL); Balasundar Iyyavu Raju, Eindhoven (NL); Shougang Wang, Eindhoven (NL); Shiwei Zhou, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 649 days.

(21) Appl. No.: 15/514,003

(22) PCT Filed: Sep. 22, 2015

(86) PCT No.: PCT/EP2015/071625
§ 371 (c)(1),
(2) Date: Mar. 24, 2017

(87) PCT Pub. No.: WO2016/046140
PCT Pub. Date: Mar. 31, 2016

(65) Prior Publication Data
US 2017/0273659 A1    Sep. 28, 2017

(30) Foreign Application Priority Data

Sep. 25, 2014   (WO) ................ PCT/CN2014/087428
Dec. 10, 2014   (EP) .................................... 14197094

(51) Int. Cl.
*A61B 8/08*       (2006.01)
*G06T 7/11*       (2017.01)
(Continued)

(52) U.S. Cl.
CPC .............. *A61B 8/08* (2013.01); *A61B 8/5223* (2013.01); *G06T 7/11* (2017.01); *G06T 7/13* (2017.01);
(Continued)

(58) Field of Classification Search
CPC ......... A61B 8/08; A61B 8/5223; G06T 7/194; G06T 7/13; G06T 7/11; G06T 7/174;
(Continued)

(56) References Cited

U.S. PATENT DOCUMENTS

| 5,668,888 A | 9/1997 | Doi et al. |
| 5,816,245 A | 10/1998 | Manseur et al. |

(Continued)

FOREIGN PATENT DOCUMENTS

| WO | 2008073560 A2 | 6/2008 |
| WO | 2010134894 A1 | 11/2010 |

OTHER PUBLICATIONS

Daniel Lichtenstein et al: "The "lung point": an ultrasound sign specific to pneumothorax", Intensive Care Medicine, vol. 25, No. 10, Oct. 1, 2000 (Oct. 1, 2000), pp. 1434-1440.
(Continued)

*Primary Examiner* — Peter Luong

(57) ABSTRACT

The embodiments disclose an ultrasound system comprising: a probe configured to obtain ultrasound data relating to scanning region including at least part of a pleural interface of a lung; and a data analyzer, configured to automatically detect information for determining lung sliding and/or lung point using one or more cross correlation maps derived from the data. The embodiments also disclose a method thereof.

15 Claims, 10 Drawing Sheets

(51) Int. Cl.
*G06T 7/174* (2017.01)
*G06T 7/246* (2017.01)
*G06T 7/194* (2017.01)
*G06T 7/13* (2017.01)

(52) U.S. Cl.
CPC .............. *G06T 7/174* (2017.01); *G06T 7/194* (2017.01); *G06T 7/246* (2017.01); *G06T 2207/10016* (2013.01); *G06T 2207/10132* (2013.01); *G06T 2207/30061* (2013.01)

(58) Field of Classification Search
CPC ........... G06T 7/246; G06T 2207/10016; G06T 2207/10132; G06T 2207/30061
See application file for complete search history.

(56) References Cited

U.S. PATENT DOCUMENTS

| | | | |
|---|---|---|---|
| 6,368,286 | B1 | 4/2002 | Whitman et al. |
| 6,650,924 | B2 | 11/2003 | Kuth et al. |
| 2007/0276245 | A1 | 11/2007 | Konofagou |
| 2008/0077011 | A1 | 3/2008 | Azuma et al. |
| 2009/0149748 | A1 | 6/2009 | Lenhardt et al. |
| 2013/0184584 | A1 | 7/2013 | Berkey |
| 2013/0197370 | A1 | 8/2013 | Burlina et al. |
| 2015/0206294 | A1 | 7/2015 | Moon et al. |

OTHER PUBLICATIONS

Daniel Lichtenstein "Lung Ultrasound in the Critically Ill" Annals of Intensive Care, 2014.
Daniel Lichtenstein et al "Ultrasound Diagnosis of Occult Pneumothorax" Critical Care Med. 2005, vol. 33, No. 6, p. 1231-1238.
Demetrios Demetriades and Edward Newton, Color Atlas of Emergency Trauma, Cambridge University Press, second edition, 2011. (www.cambridge.org/9781107001527).
Philips Perera, et.al, 'Rapid ultrasound in shock: The RUSH protocol', Emergency Medicine, Apr. 2010, vol. 2010: 12-26 (www.emedmag.com).
Synho Do, et.al., 'Automated quantification of Pneumothorax in CT', Computational and Mathematical methods in Medicine, 2012, vol. 2012, Article ID 736320.
Chad G. Ball, et. al., 'The occult pneumothorax: What have we learned?', Can J Surg, 2009, vol. 52(5): E173-E179.
BS. Ku, et. al., 'Clinician-performed bedside ultrasound for the diagnosis of pneumothorax', West Journal of Emergency Medicine, 2013, vol. 14(2):103-108.
A. Khaled, et. al., 'The characteristics of ultrasonography for the detection of pneumothorax: A systematic review and Meta-analysis', Chest , 2012, vol. 141(3): 703-709.
N.P. Oveland, et.al, 'The ontrapleural volume threshold for ultrasound detection of pneumothoraces: An experimental study on porcine models', Scandianaian Journal of Trauma, Resuscitation and Emergency Medicine, 2013, 21:11 (http://www.sjtrem.com/content/21/1/11.
P.D. Levy, et. al., 'Micro-power impulse radar: A novel technology for rapid real-time detection of pneumothorax', Emergency Medicine International, 2011, vol. 2011.
R. G. Wilkerson, et. al., 'Sensitivity of bedside ultrasound and supine anteroposterior chest radiographs for the identification of pneumothorax after blunt trauma', Academic emergency medicine, 2010, vol. 17:11-17.
Y. Moriwaki, et. al., 'Ultrasonography for the diagnosis of intraperitoneal free air in chest-abdominal-pelvic blunt trauma and critical acute abdominal pain', Arch Surgery, 2009, 144(2):137-141.
G. Volpicelli et. al , 'International evidence-based recommendations for point-of-care lung ultrasound', Intensive Care Medicine, 2012, 38:577-591.

DEVICE AND METHOD FOR AUTOMATIC PNEUMOTHORAX DETECTION

This application is the U.S. National Phase application under 35 U.S.C. § 371 of International Application No. PCT/EP2015/071625, filed on Sep. 22, 2015, which claims the benefit of Application Serial No. PCT/CN2014/087428 filed Sep. 25, 2014 and EP 14197094.7, filed Dec. 10, 2014, 2014. These applications are hereby incorporated by reference herein.

TECHNICAL FIELD

Example embodiments of the present disclosure generally relate to automatic detection of lung related ailments or conditions, and more specifically to a system and method for detecting pneumothorax automatically using ultrasound imaging systems.

BACKGROUND

Chest trauma accounts for 20% of all trauma cases in the world. Chest trauma is estimated to be the primary cause of death in 25% of traumatic mortalities and a contributing factor in another 25% of deaths. Early detection and timely selection of the appropriate investigations and treatments are all critical components for optimal outcome. Ultrasound imaging is widely used for the initial diagnosis to evaluate patients with blunt thoracic trauma. Identifying or detecting pneumothorax (PTX) is critically important in making an accurate diagnosis and is considered a key feature to be detected.

At present, PTX detection approaches using ultrasound are based on visual observations of images following the Bedside Lung Ultrasound in Emergency (BLUE or its updated version) protocol, which are time consuming and dependent on operators' experiences. For inexperienced ultrasound operators, the detecting sensitivity is only 57%, compared to 91% for well-trained and experienced operators. The ultrasound detection of PTX is the most difficult part of training: much experience is required to acquire appropriate skills to recognize lung sliding and its abolition. The detection is even more difficult in the presence of partial PTX or small PTX. The patient should lie strictly supine to allow location of pleural gas effusion in non-dependent lung regions. The major problem for detecting PTX via ultrasound is the need for advanced training, and its accuracy is highly operator dependent.

WO 2006/044996 A2 discloses system and method for the automatic detection of the boundary of a structure in an ultrasound image. The method includes providing a matrix of pixel values corresponding to the image. An autocorrelation calculation is performed on the matrix of pixel values to generate a new, correlation matrix to emphasize the difference in echogenicity between the structure and the surrounding image.

SUMMARY

Therefore, it is an object to solve at least one of the above-mentioned problems.

According to one aspect of the embodiments, there is provided an ultrasound system for scanning a lung of a subject comprising: a probe configured to obtain a sequence of temporal frames of ultrasound data relating to a scanning region including at least part of a pleural interface of a lung, each temporal frame of ultrasound data at least extending along a range direction of the probe; and a data analyzer, comprising a processing circuitry, and configured to derive one or more than one cross correlation maps, each cross correlation being derived from a pair of temporal frames of the sequence of temporal frames, to filter the one or more than one cross correlation maps to obtain one or more than one filtered cross correlation maps, and to identify, in the one filtered cross correlation map or a compounded version of the more than one filtered cross correlation maps, a first boundary at which a value change along the range direction exceeds a first predetermined threshold.

It is well known that the cross correlation map derived from a pair of temporal frames represents the dependency between a region (such as a point or a set of points) in one frame of the pair and a corresponding region in the other frame of the pair, whilst an autocorrelation map represents the dependency among the ultrasound data of different regions of the same frame itself or energy of the frame. Without specifying otherwise, the correlation used throughout this document always refers to cross correlation.

The time internal of the pair of temporal frames can be set in various way. For example, each pair may have a first time interval (which could be the same or varied among pairs) between the temporal frames of the pair, and may have a second time interval (which could be the same or varied among pairs) to an adjacent pair.

In an embodiment, the identified first boundary is presented to the user via a user interface such as a display.

In another embodiment, the identified first boundary can be used for further processing. For example, lung sliding is detected as being present if the first boundary is identified, and an indicator for indicating the existence of lung sliding may be presented to the user via visual output and/or audio output. The detection of lung siding is further known to assist the detection of pneumothorax. If the lung sliding is identified in at least one part of the scanning region, no pneumothorax is determined to be present in the at least one part of the scanning region. However, if there is no lung sliding, but lung points have been detected, then it can be determined that PTX is present in this scanning region.

It is well-known in the field of ultrasound imaging that compounding can be a coherent combination, either spatially or temporally.

The cross correlation map can be a temporal cross correlation coefficient (i.e. CC) map a normalized cross correlation coefficient (i.e. NCC) map of two temporal frames.

Conventionally, PTX detection relies on the manual observation of the B-mode ultrasound image by the clinician staff. Although PTX detection is supposed to be observable and possible for experienced users showing a sensitivity of 91%, it is not always easily detectable by the emergency clinician staffs, especially inexperienced users showing a sensitivity of 57%. With the aforementioned approach, lung sliding can be easily observed by users and/or automatically detected based on the correlation maps of the sequence of temporal frames.

If the first boundary is identified, the pleural interface of the lung is considered to at least partly locate at the first boundary. The inventors of the present invention recognize that in case of the normal lung, the part of the region above the pleural line (i.e. near to the skin) exhibits relatively less motion and thus high correlation, whilst the part of the region below the pleural line exhibits low correlation, and therefore, the pleural interface of the lung at least partly lies at the first boundary which is identified as an interface between the part of the region with high correlation and the part of the region with low correlation. The pleural line is known as a boundary between the lung tissue and the air in the lung. Unlike tissue or liquid such as blood, almost no ultrasound signal can transmit through the air and the ultrasound data for a region containing air will be quite random, resulting in that the cross correlation in the region below the pleural line is low. Such a CC pattern for a normal lung is called high-to-low. In case of PTX, the correlation of the whole region will be similarly high, and the CC pattern for the PTX case is called high-to-high, and therefore the first boundary cannot be identified from the correlation map. In case of partial PTX, part of the region where the first boundary is identified is a normal, high-to-low CC pattern, whilst part of the region where the first boundary is not identified is an abnormal, high-to-high CC pattern. The point between two pattern changes is referred to as lung point.

According to some embodiments, the data analyzer is further configured to derive one or more than one ultrasound data maps, each ultrasound data map being derived from one temporal frame or a compounded version of more than one temporal frames of the sequence of temporal frames; filter the one or more than one ultrasound data maps to obtain one or more than one filtered ultrasound data maps; and to identify the first boundary from the one filtered ultrasound data map or a compounded version of the more than one filtered ultrasound data maps in combination with the one filtered cross correlation map or a compounded version of the more than one filtered cross correlation maps.

With the use of both one or more ultrasound data maps each derived from an individual temporal frame and a cross correlation map derived from a pair of temporal frames, the accuracy of the identification of the first boundary can be further improved.

The cross correlation map or the ultrasound data map is built using amplitude data extracted from the ultrasound data. The ultrasound data can comprise radio frequency data, and, more generally, fundamental ultrasound image data or harmonic ultrasound image data. The ultrasound data can be obtained from pulse inversion of radio frequency data in the tissue harmonic imaging mode or radio frequency data can be obtained in the fundamental imaging mode.

In an embodiment, the ultrasound data map is a short time energy map and thus can be the conventional B-mode ultrasound image.

According to some embodiments, to identify the first boundary, said data analyzer further comprises: identifying a boundary line comprising a point from each line of a plurality of scanning lines, at which point a value change along the scanning line exceeds a first predetermined threshold in the one filtered cross correlation map or a compounded version of the more than one filtered cross correlation maps; identifying a starting point as a point at which there is a value increase on the boundary line in the one filtered ultrasound data map or the compounded version of the more than one filtered ultrasound data maps, which value increase exceeds a second predetermined threshold, and identifying an end point as a point at which there is a value decrease on the boundary line in the one ultrasound data map or the compounded version of the more than one filtered ultrasound data maps, which value decrease exceeds a third predetermined threshold. The first boundary is identified as the part of the boundary line between the starting point and the end point.

For example, to identify the boundary line, the data analyzer is configured to search for such a point along each line of the plurality of scanning line that a value change along the scanning line exceeds, at the point, the first predetermined threshold in the one filtered cross correlation map or a compounded version of the more than one filtered cross correlation maps, and all obtained such points form the boundary line.

According to some embodiments, the data analyzer is further configured to determine motion of the identified first boundary, based on a normalized cross correlation function of the sequence of the temporal frames.

It is well-known in the field of ultrasound imaging that the normalized cross correlation function indicates the cross correlation (also called normalized cross correlation coefficient) of the ultrasound data at a corresponding point in the sequence of the temporal frames as a function of time as well as the relative displacement of the corresponding point in the sequence of the temporal frames.

The determined motion of the identified first boundary can be presented to the user via a user interface. Additionally or alternatively, the data analyzer can be further configured to use the determined motion of the identified first boundary for further processing.

In this way, quantification of the motion of at least part of a pleural interface can be achieved.

In some embodiments, at least one of displacement and velocity of the identified interface is determined.

In some embodiments, the motion of the identified first boundary along a direction orthogonal to the range direction of the probe is determined.

As is well-known, the face of the probe, being in contact with the skin, is usually a rectangle, where the long direction is generally referred to as the "azimuth" direction and the orthogonal direction is generally referred to as the "elevation" direction. Furthermore, the field of view of the probe extends in the "range" direction. In other words, the range direction represents the propagation direction of ultrasound signals, also known as depth direction of the ultrasound data. Since the range direction is orthogonal to the face of the probe and therefore orthogonal to both the azimuth and elevation directions, the range direction is also known as the longitudinal direction of the ultrasound probe. The ultrasound frame extends at least along the range direction of the probe. In some embodiments, the ultrasound frame is two dimensional and extends, for example, along a further direction other than the range direction of the probe, such as the azimuth direction. In some other embodiments, the ultrasound frame is three dimensional, and extends in both azimuth direction and elevation direction in additional to the range direction.

According to some embodiments, to determine motion of the first boundary, the data analyzer is further configured to determine a first region covering the whole first boundary, and to determine motion of the first region in the sequence of the temporal frames.

According to some embodiments, to determine motion of the first boundary the data analyzer is further configured to determine a second region containing only background soft tissue which is closer to the probe than the first boundary, and to determine the relative motion between the first and the second region as the motion of the first boundary. Using the relative motion, the negative impact of the undesired movement, e.g. caused by slight movement between the probe and the scanning region (i.e. the region to be scanned), can be reduced.

According to some embodiments, the data analyzer is further configured to identify, in the one filtered cross correlation map or a compounded version of the more than one filtered cross correlation maps, a second boundary at which a value change along a direction orthogonal to the range direction exceeds a fourth predetermined threshold. In other words, the second boundary is identified as a boundary at which the cross correlation value changes from high to low, or vice versa along the direction orthogonal to the range direction.

In an embodiment, the identified second boundary is presented to the user via a user interface such as a display.

In another embodiment, the identified second boundary can be used for further processing. For example, the lung point is detected based on the identified second boundary. The detected lung point can be presented to the user via a user interface. Additionally or alternatively, the data analyzer can be further configured to use the detected lung point for further processing.

According to another aspect of the embodiments, there is provided a method of scanning a lung of a subject using ultrasound, comprising: obtaining a sequence of temporal frames of ultrasound data relating to a scanning region including at least part of a pleural interface of the lung, each temporal frame of ultrasound data at least extending along a range direction of the probe; deriving one or more than one cross correlation maps, each from a pair of temporal frames of the sequence of temporal frames, each pair having a same time interval between the temporal frames of the pair; filtering the one or more than one cross correlation maps to obtain one or more than one filtered cross correlation maps; and identifying, in the one filtered cross correlation map or a compounded version of the more than one filtered cross correlation maps, a first boundary at which a value change along the range direction exceeds a first predetermined threshold.

According to another aspect of the embodiments, there is provided an ultrasound system for scanning a lung of a subject, comprising: a probe configured to obtain a sequence of temporal frames of ultrasound data relating to a region including at least part of a pleural interface of the lung, each temporal frame of ultrasound data at least extending along a range direction of the probe; and a data analyzer, comprising: a map deriver configured to derive one or more than one cross correlation maps, each from a pair of temporal frames of the sequence of temporal frames, each pair having a same time interval between the temporal frames of the pair; a map filter configured to filter the one or more than one cross correlation maps to obtain one or more than one filtered cross correlation maps; a pleural interface identifier configured to identify, in the one filtered cross correlation map, or in a compounded version of the more than one filtered cross correlation maps, a first boundary at which a value change along the range direction exceeds a first predetermined threshold.

BRIEF DESCRIPTION OF THE DRAWINGS

The technology will now be described, by way of example, based on embodiments with reference to the accompanying drawings, wherein.

DETAILED DESCRIPTION OF THE EMBODIMENTS

Figure 1:
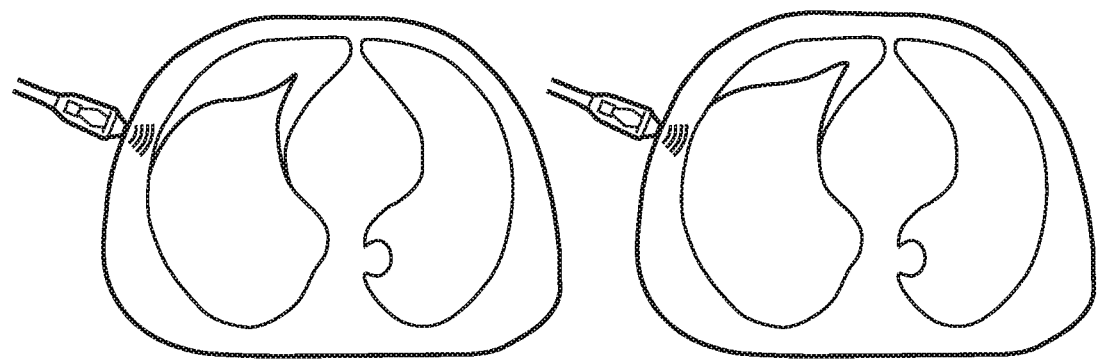
FIG. 1 illustrates a diagram explaining the origin of the "Lung Point"

Embodiments herein will be described in detail hereinafter with reference to the accompanying drawings, in which embodiments are shown. These embodiments may, however, be embodied in many different forms and should not be construed as being limited to the embodiments set forth herein. The elements of the drawings are not necessarily to scale relative to each other. Like numbers refer to like elements throughout.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood. It will be further understood that terms used herein should be interpreted as having a meaning that is consistent with their meaning in the context of this specification and the relevant art and will not be interpreted in an idealized or overly formal sense unless expressly so defined herein.

The present technology is described below with reference to block diagrams and/or flowchart illustrations of methods, apparatus (systems) and/or computer program products according to the present embodiments. It is understood that blocks of the block diagrams and/or flowchart illustrations, and combinations of blocks in the block diagrams and/or flowchart illustrations, may be implemented by computer program instructions. These computer program instructions may be provided to a processor, controller or controlling unit of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

Embodiments herein will be described below with reference to the drawings.

As indicated above, some example embodiments may enable the provision of a mechanism by means of which it is possible to detect pneumothorax automatically on the basis of machine-executed analysis of ultrasound data of lungs. In some cases, the data may be one-dimensional, two-dimensional or three-dimensional Radio Frequency (RF) signals or video imagery that may be obtained by real-time imaging modalities such as preferably ultrasound. The data may be analyzed to identify or locate at least part of the pleural interface as a region of interest (ROI). The ROI may then be further analyzed to determine whether indications of pleural sliding are present. Besides, the data may be analyzed to determine whether lung points are present. Thereafter, a determination could be made regarding the presence and size of a pneumothorax.

The lungs are located in the thoracic cavity of the chest, and are essential to respiration. Each lung is somewhat triangular in shape with the apex being superior and the base being inferior. The lungs are formed of a relatively light and porous material and are maintained at a pressure that is below atmospheric pressure. The lungs are separated from the abdominal cavity by a muscular diaphragm located at the base of the lungs. The diaphragm moves to draw air into and expel air from the lungs.

The lungs are surrounded by a double-walled sac called the pleura. The pleura includes visceral and parietal pleura membranes that have a thin space between them which is referred to as pleural cavity or pleural interface. The pleural interface normally includes a very small amount of pleural fluid to enable the lungs to expand and contract without adherence between the membranes. The pleural interface therefore typically enables the visceral and parietal pleura membranes to slide back and forth relative to each other during normal respiration. This phenomenon is referred to as "lung sliding". Evidence of lung sliding is considered to be evidence of normal lung function ruling out the existence of a pneumothorax. A pneumothorax is indicated by an air pocket (or so-called gas pocket) forming in the pleural interface, which may prevent lung sliding at the position of the air pocket. Thus, if absence of lung sliding is detected in a particular region, there is a strong possibility that a pneumothorax may be occurring in the particular region.

Pneumothorax is defined by the interposition of an air/gas pocket between visceral and parietal pleural layers. Since the air pocket in the pleural space moves anterior and the lung collapses to a dependent position posteriorly, there is a point, usually in the lateral regions where the normal lung and the air pocket may be visualized in the same view. As is shown in FIG. 1, on moving from anterior to lateral, a pneumothorax pattern gives way to a fleeting appearance of lung pattern in a particular location of the chest wall. At the border of the pneumothorax (where the probe is directed at, as shown in FIG. 1), pleural layers start to contact one another during inspiration (lung itself is located in front of the probe, which remained motionless at the site of examination) with normal lung sliding, and during expiration the pleural layers are separated again. The point where such a phenomenon occurs is referred to as a "lung point". More information about lung point can be found in "EMERGENCY SONOGRAPHY FOR TRAUMA FAST PROTOCOL" by SONOMOIR, 2011. A lung point is considered to be evidence of a pneumothorax.

Penetrating trauma or blunt trauma can cause pneumothorax. Moreover, the presence of these types of top-level injuries may make it more difficult to detect pneumothorax. Additionally, an initially small pneumothorax may progress into more serious states if left untreated, which may cause significant morbidity and mortality later. Particularly in the fields of emergency and trauma medicine, an automatic method of detecting pneumothorax may be useful in avoiding delayed detection or in avoiding failure to arrive at a detection relative to instances of pneumothorax. Accordingly, some example embodiments may provide an ultrasound system that is capable of providing automatic detection of pneumothorax.

Figure 2:
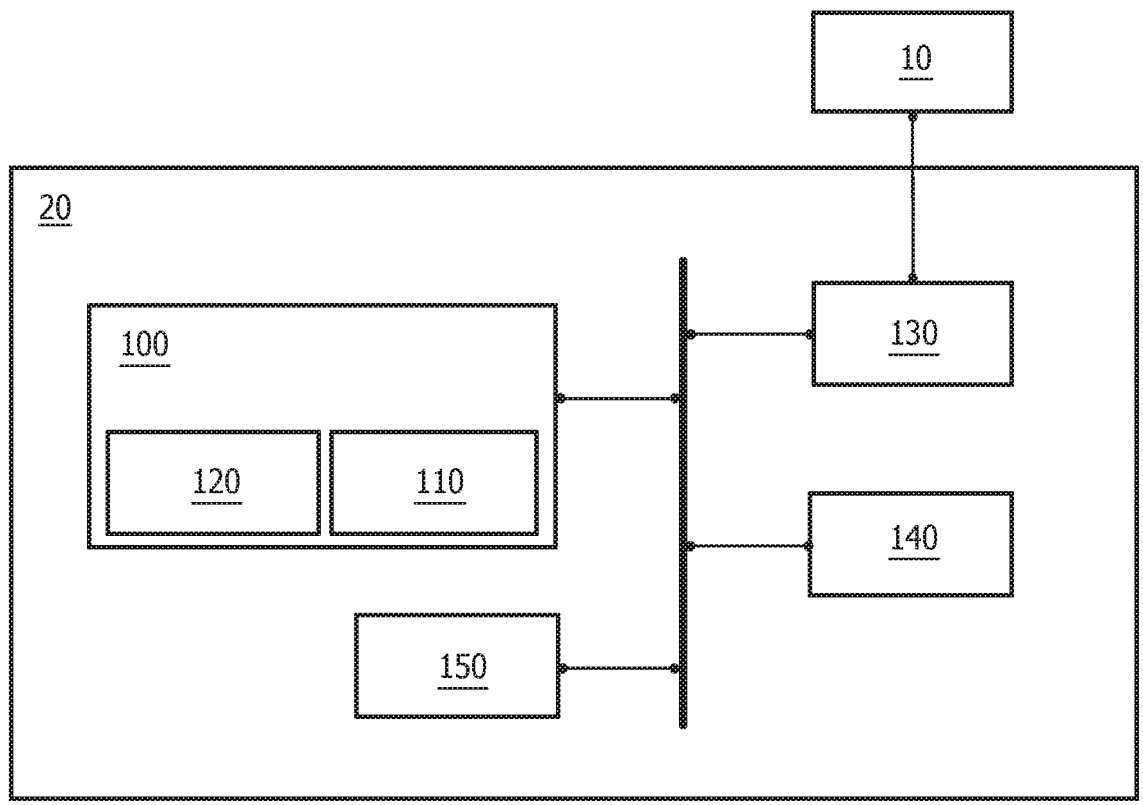
FIG. 2 illustrates a block diagram of an ultrasound system of one example embodiment.

FIG. 2 illustrates a block diagram of an ultrasound system of one example embodiment. In this example, the ultrasound system is embodied as a computer controlled device. Thus, for example, the ultrasound system may include a probe 10 and a data analyzer 20. The probe 10 may be an imaging device configured to obtain data of the lungs of a subject. The collectable data may be captured non-invasively by acquiring data using an ultrasound probe that remains external to the body, but that measures ultrasound waves that pass through and/or reflect off of various body parts. In some cases, the probe 10 may generate Radio Frequency signals and/or video data comprising a series of frames. In an example embodiment, the probe 10 may be embodied as or include real-time imaging modalities such as, preferably, ultrasound. Ultrasound, in particular, may provide a relatively low cost, low power, portable modality that can be employed in emergency and trauma environments without employing ionizing radiation.

The probe 10 may provide data to the data analyzer 20, which may be configured to receive and process data captured by the probe 10 in order to generate results that may be used to detect various lung conditions including pneumothorax. In some cases, the data analyzer 20 may receive the data in real time (or near real time) directly from the probe 10. However, in other cases, data from the probe 10 may be stored first, and, at a later point in time, may be retrieved from storage before being analyzed by the data analyzer 20.

As shown in FIG. 2, the data analyzer 20 may include, or be in communication with, processing circuitry 100 that is configurable to perform actions in accordance with example embodiments described herein. As such, for example, at least some of the functions attributable to the data analyzer 20 may be carried out or instructed by the processing circuitry 100. The processing circuitry 100 may therefore provide the hardware for hosting software to configure the system for machine learning and machine driven analysis techniques consistent with example embodiments. Detection and delineation of lung conditions such as, for example, pneumothorax may then be accomplished using the processing circuitry 100.

The processing circuitry 100 may be configured to perform data processing, control function execution and/or other processing and management services according to an example embodiment of the present invention. In some embodiments, the processing circuitry 100 may be embodied as a chip or chip set. In other words, the processing circuitry 100 may comprise one or more physical packages (e.g., chips) including materials, components and/or wires on a structural assembler (e.g., a baseboard).

In an example embodiment, the processing circuitry 100 may include one or more instances of a processor 110 and memory 120 that may be in communication with, or otherwise control, a device interface 130 and, in some cases, a user interface 140. As such, the processing circuitry 100 may be embodied as a circuit chip (e.g., an integrated circuit chip) configured (e.g., with hardware, software or a combination of hardware and software) to perform operations described herein.

The user interface 140 (if implemented) may be in communication with the processing circuitry 100 to receive an indication of a user input at the user interface 140 and/or to provide an audible, visual, mechanical or other output to the user. As such, the user interface 140 may include, for example, a display, one or more buttons or keys (e.g., function buttons), and/or other input/output mechanisms (e.g., keyboard, microphone, speakers, cursor, joystick, lights and/or the like). The user interface 140 may display information indicating an identity or certain characteristics of a data set (e.g., including raw RF data or results of analyzing the raw RF data) being processed by the data analyzer 20. The characteristics of the data set may then be processed and information associated therewith may be presented on a display of the user interface 140, based on instructions executed by the processing circuitry 100 for the analysis of the data according to prescribed methodologies and/or algorithms. Moreover, in some cases, the user interface 140 may include options for selection of one or more reports to be generated based on the analysis of a given data set.

The device interface 130 may include one or more interface mechanisms for enabling communication with other external devices (e.g., the probe 10) or internal functional components of the data analyzer 20. In some cases, the device interface 130 may be any means such as a device or circuitry embodied in either hardware or a combination of hardware and software that is configured to receive and/or transmit data from/to devices in communication with the processing circuitry 100.

In an example embodiment, the memory 120 may include one or more non-transitory memory devices such as, for example, a volatile and/or non-volatile memory that may be either fixed or removable. The memory 120 may be configured to store information, data, applications, instructions or the like for enabling the data analyzer 20 to carry out various functions in accordance with example embodiments of the present invention. For example, the memory 120 could be configured to buffer input data for processing by the processor 110. Additionally or alternatively, the memory 120 could be configured to store instructions for execution by the processor 110. As yet another alternative, the memory 120 may include one or more databases that may store a variety of data sets such as data obtained from the probe 10, short-time energy maps, correlation maps and/or the like to be employed for the execution of example embodiments. Among the contents of the memory 120, applications may be stored for execution by the processor 110 in order to carry out the functionality associated with each respective application. In some cases, the applications may include instructions for control of the data analyzer 20 to generate and/or employ analytical tools for analyzing data to identify ROI and analyze data therein to determine whether a pneumothorax has occurred in the ROI. In some cases, the applications may further include instructions for generating outputs and/or reports associated with analysis of patient data as described herein.

The processor 110 may be embodied in a number of different ways. For example, the processor 110 may be embodied as any one of various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 110 may be configured to execute instructions stored in the memory 120 or otherwise accessible to the processor 110. As such, whether configured by hardware or by a combination of hardware and software, the processor 110 may represent an entity (e.g., physically embodied in circuitry in the form of processing circuitry 100) capable of performing operations according to example embodiments of the present invention while being configured accordingly. Thus, for example, when the processor 110 is embodied as an ASIC, FPGA or the like, the processor 110 may be specifically configured hardware for conducting the operations described herein. Alternatively, as another example, when the processor 110 is embodied as an executor of software instructions, the instructions may specifically configure the processor 110 to perform the operations described herein.

In an example embodiment, the processor 110 (or the processing circuitry 100) may be embodied as, include or otherwise control, the data analyzer 20. As such, in some embodiments, the processor 110 (or the processing circuitry 100) may be said to cause each of the operations described in connection with the data analyzer 20 by directing the data analyzer 20 to undertake the corresponding functionalities responsive to execution of instructions or algorithms configuring the processor 110 (or processing circuitry 100) accordingly.

In an example embodiment, data captured in association with ultrasound scanning of the lungs of a particular patient may be stored (e.g., in the memory 120) or passed directly to the data analyzer 20. Thereafter, the data may be processed by the data analyzer 20 to enable the processing circuitry 100 to process the data in real time (or near real time) or to process the data as the data is extracted from the memory. The processor 110 may be configured to locate the pleural interface, determine whether lung sliding is occurring at the pleural interface, whether a lung point exists, and make a determination regarding the existence of a pneumothorax based on the determination as to whether sliding is occurring and/or a lung point exists, etc.

In one embodiment, the probe 10 is configured to obtain a sequence of temporal frames of ultrasound data relating to a region including at least part of a pleural interface of a lung.

Figure 3:
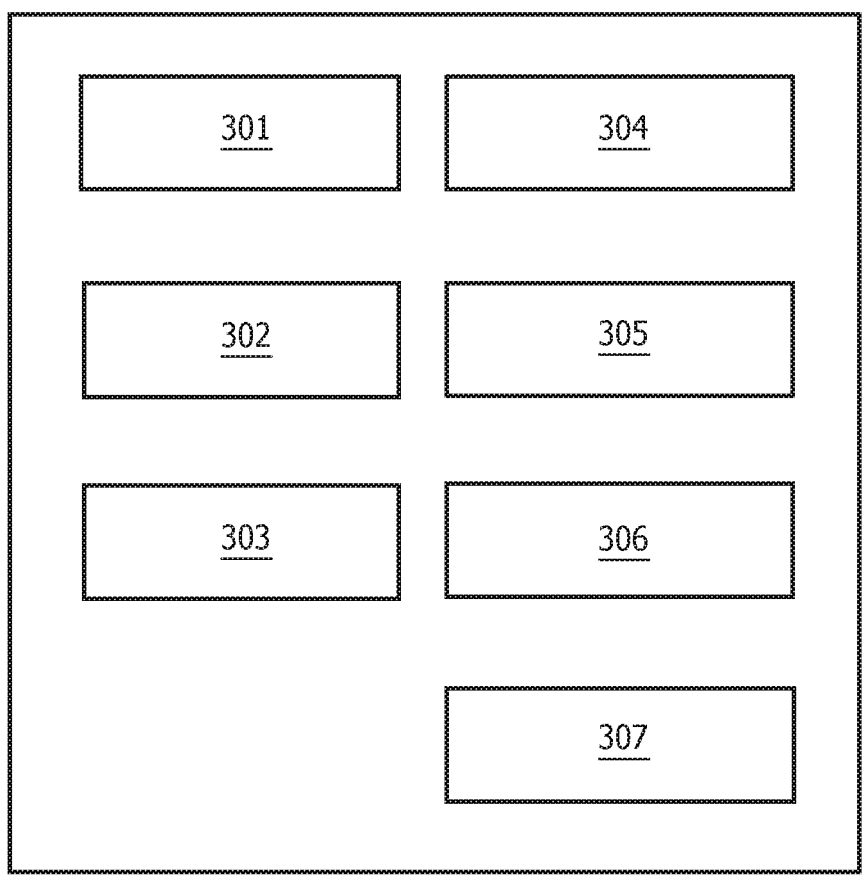
FIG. 3 illustrates a block diagram of a component in the ultrasound system of one example embodiment.

In an example embodiment, the processor 110 further includes a map deriver 301, a map filter 302, a pleural interface identifier 303, a motion detector 304, a lung point detector 305, a PTX determiner 306, and a PTX quantifier 307, shown in FIG. 3.

The map deriver 301 is configured to derive one ultrasound data map from any of two frames of the ultrasound data, or derive more ultrasound data maps from the more than two frames of the ultrasound data, and derive one correlation map from the two frames of the ultrasound data, or derive more than one correlation map, each being derived from a pair of temporal frames of the more than two frames of ultrasound data, each pair having a first time interval (which could be the same or varied among pairs) between the temporal frames of the pair, and have a second time interval (which could be the same or varied among pairs) with respect to an adjacent pair.

The map filter 302 is configured to filter the more than one ultrasound data maps and one or more correlation maps to obtain more than one filtered ultrasound data maps and one or more filtered correlation maps.

The boundary identifier 303 is configured to identify a boundary line, comprising a point along each line of a plurality of scanning lines, and at such point a value change along the scanning line exceeds a first predetermined threshold in the one filtered correlation map or a compounded version of the more than one filtered correlation maps; and to identify a start point as a point at which there is a value increase on the boundary line in the one filtered ultrasound data map or the compounded version of the more than one filtered ultrasound data maps, which value increase exceeds a second predetermined threshold; and identifying an end point as a point at which there is a value decrease on the boundary line in the one of the ultrasound data map or the compounded version of the more than one filtered ultrasound data maps, which value decrease exceeds a third predetermined threshold.

The identification of the first boundary can indicate the existence of lung sliding.

The motion detector 304 is configured to determine motion of the identified first boundary, based on a normalized correlation function of the sequence of the temporal frames. To determine motion of the identified first boundary, the motion detector is further configured to: determine a first region covering the first boundary; and determine motion of the first region as motion of the first boundary. Alternatively or additionally, to determine motion of the identified first boundary, the motion detector is further configured to: determine a second region containing only background soft tissue which is closer to the probe than the first boundary; and determine the relative motion between the first and the second region as the motion of the first boundary.

The lung point detector 305 is configured to identify, in the one filtered correlation map or a compounded version of the more than one filtered correlation map, a second boundary at which a value change along a direction orthogonal to the range direction of the probe exceeds a fourth predetermined threshold, and to determine a lung point, based on the second boundary if the second boundary is identified.

The PTX determiner 306 is configured to determine whether a pneumothorax is present, based on the identification of the first boundary, the determined motion of the first boundary and/or the determination of lung point existence.

The PTX quantifier 307 is configured to estimate the relative size of the PTX, for example, 30%, 70%, etc., which is a commonly used parameter in PTX detection. The relative size can be determined by the ratio of the volume of a pneumothorax to that of a cavity formed in the pleural interface. For example, the contour of the pneumothorax is outlined by ascertaining lung points at different intercostal spaces and subsequently lining up those lung points, and in turn, the volume of the pneumothorax can be estimated based on the contour, using mathematical models and calculations. Similarly, the volume of the lung can be estimated approximately, based on the contour of the pleural interface, or it can be estimated using data from other sources.

In an alternative example embodiment, the data analyzer 20 may include a pneumothorax (PTX) detector 150 that may be configured to locate the pleural interface, determine whether sliding is occurring at the pleural interface, whether a lung point exists, and make a determination regarding the existence of a pneumothorax, based on the determination as to whether lung sliding is occurring or a lung point exists, etc.

In an example embodiment, the PTX detector 150 may be any means, such as a device or circuitry embodied in either hardware, or a combination of hardware and software, that is configured to perform the corresponding functions of the PTX detector 150 as described herein under the control of the processing circuitry 100. In an example embodiment, the PTX detector 150 may be configured to perform various actions associated with determining a pneumothorax detection result relative to a particular location being examined.

In an alternative example embodiment, the PTX 150 further includes a map deriver 301, a map filter 302, a pleural interface identifier 303, a motion detector 304, a lung point detector 305, a PTX determiner 306, and a PTX quantifier 307, shown in FIG. 3.

The map deriver 301 is configured to derive one ultrasound data map from any of two frames of the ultrasound data, or derive more ultrasound data maps from the more than two frames of the ultrasound data, and derive one correlation map from the two frames of the ultrasound data, or derive more than one correlation map, each being derived from a pair of temporal frames of the more than two frames of ultrasound data, each pair having a first time interval (which could be the same or varied among pairs) between the temporal frames of the pair, and a second time interval (which could be the same or varied among pairs) with respect to an adjacent pair.

The map filter 302 is configured to filter the more than one ultrasound data maps and one or more correlation maps to obtain more than one filtered ultrasound data maps and one or more filtered correlation maps.

The boundary identifier 303 is configured to identify a boundary line composed by many points of each line of a plurality of scanning lines, to determine at which point a value change along the scanning line exceeds a first predetermined threshold in the one filtered correlation map or a compounded version of the more than one filtered correlation maps; and identify a start point as a point at which there is a value increase on the boundary line in the one filtered ultrasound data map or the compounded version of the more than one filtered ultrasound data maps, which value increase exceeds a second predetermined threshold, and identify an end point as a point at which there is a value decrease on the boundary line in the one ultrasound data map or the compounded version of the more than one filtered ultrasound data maps, which value decrease exceeds a third predetermined threshold. The identification of the first boundary indicates the existence of lung sliding.

The motion detector 304 is configured to determine motion of the identified first boundary, based on a normalized correlation function of the sequence of the temporal frames. To determine motion of the identified first boundary, the motion detector is further configured to: determine a first region covering the first boundary; and determine motion of the first region as motion of the first boundary. Alternatively or additionally, to determine motion of the identified first boundary, the motion detector is further configured to: determine a second region containing only background soft tissue which is closer to the probe than the first boundary; and determine the relative motion between the first and the second region as the motion of the first boundary.

The lung point detector 305 is configured to identify, in the one filtered correlation map or a compounded version of the more than one filtered correlation map, a second boundary at which a value change along a direction orthogonal to the range direction of the probe exceeds a fourth predetermined threshold, and to determine a lung point based on the second boundary if the second boundary is identified.

The PTX determiner 306 is configured to determine whether a pneumothorax is present, based on the identification of the first boundary, the determined motion of the first boundary and/or the determination of lung point existence. The PTX quantifier 307 is configured to estimate relative size, for example, 30%, 70%, etc., which is a commonly used parameter in PTX detection. The relative size can be determined by the ratio of the volume of a pneumothorax to that of a cavity formed in the pleural interface. For example, the contour of the pneumothorax is outlined by ascertaining lung points at different intercostal spaces and lining up those lung points, and in turn, the volume of the pneumothorax can be estimated based on the contour, using mathematical models and calculations. Similarly, the volume of the lung can be estimated approximately, based on the contour of the pleural interface, or it can be estimated using data from other sources.

In the above two embodiments:

For example, in the sequence of temporal frames {F1, F2, ..., FN}, F1 and F3 could be used to derive the first correlation map, F2 and F4 could be used to derive the second correlation map, F3 and F5 could be used to derive the third correlation map. Alternatively, F1 and F3 could be used to derive the first correlation map, F2 and F4 could be used to derive the second correlation map, F5 and F7 could be used to derive the third correlation map. Alternatively, F1 and F3 could be used to derive the first correlation map, F5 and F9 could be used to derive the second correlation map, F10 and F13 could be used to derive the third correlation map.

It will be appreciated that the frame rate can be moderate so that the pair can be made up of two adjacent frames and there will not be much redundancy.

It will also be appreciated that if the frame rate is high, then two temporal frames with an interval of two or more frames could be used to derive the correlation map. For example, in the sequence of temporal frames {F1, F2, ..., FN}, F1 and F3 could be used to derive the first correlation map, F2 and F4 could be used to derive the second correlation map. Alternatively, F1 and F3 could be used to derive the first correlation map, F4 and F6 could be used to derive the second correlation map.

It should also be appreciated that the ultrasound data map could be a short time energy (STE) map. As a STE map is obtained once the amplitude is obtained and involves no quantization and coding, it is more computation efficient.

It should also be appreciated that the correlation can be calculated from temporal frames that are signals processed from received echo signals in various ways, such as bandpass filtering, decimation, I and Q component separation, and harmonic signal separation, which acts to separate linear and nonlinear signals so as to enable the identification of nonlinear (higher harmonics of the fundamental frequency) echo signals returned from the body.

It will be appreciated by one skilled in the art that the compounded version could be a coherent superposition of the more than one filtered correlation maps.

The elements shown in FIG. 2 and FIG. 3 are illustrated as separate elements. However, this is merely to indicate that the functionalities are separated. The elements can be provided as separate hardware devices. However, other arrangements are possible, such as the map deriver 301 and the map filter 302 can be physically combined into one unit. Any combination of the elements can be implemented in any combination of software, hardware, and/or firmware in any suitable location. For example, there could be one map deriver for deriving ultrasound data maps and another, separately configured, map deriver for deriving correlation maps.

Some of the elements may constitute machine-executable instructions embodied within a machine, e.g., readable medium, which when executed by a machine will cause the machine to perform the operations described. Besides, any of the elements may be implemented as hardware, such as an application specific integrated circuit (ASIC), Digital Signal Processor (DSP), Field Programmable Gate Array (FPGA) or the like.

Besides, it should be understood that the arrangements described herein are set forth only as examples. Other arrangements and elements (e.g., more input units, more output units, transceivers, etc.) can be used in addition to or instead of those shown, and some elements may be omitted altogether.

Functionalities and cooperation between those elements are described in detail with reference to FIG. 4.

Figure 4:
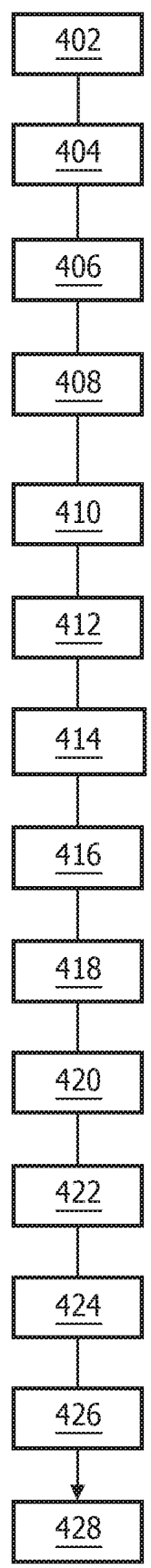
FIG. 4 illustrates a flowchart of a detection method of one example embodiment.

FIG. 4 illustrates a flowchart of a detection method of one example embodiment. It will be understood that each block of the flowchart, and combinations of blocks in the flowchart, may be implemented by various means, such as hardware, firmware, processor(s), circuitry and/or other devices associated with the execution of software including one or more computer program instructions. For example, one or more of the procedures described may be embodied by computer program instructions. In this regard, the computer program instructions which embody the procedures described above may be stored by a memory and executed by a processor. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method of determining the presence of a pneumothorax according to an example embodiment of the invention is shown in FIG. 4. The method of FIG. 4 may entirely, with the exception of operation 402, or at least in part, be executed automatically (e.g., without operator interaction to initiate each step or the series of steps) by processing circuitry 100. The method may include obtaining a sequence of frames of ultrasound data relating to a scanning region including at least part of a pleural interface of lungs at operation 402. The data may include at least two frames.

In one example embodiment, the method further comprises deriving one ultrasound data map from any of the two frames of ultrasound data, and then deriving one correlation map from each of the two frames of ultrasound data at operation 404, for example in the map deriver 301, filtering the one ultrasound data map and the correlation map to obtain one filtered ultrasound data map and one filtered correlation map at operation 406, for example in the map filter 302, identifying, in the one filtered correlation map, a first boundary at which a value change along a range direction of the probe exceeds a first predetermined threshold at operations 408 and 410 all together for example in the boundary identifier 303, determining motion of the identified first boundary, based on a normalized correlation function of the two temporal frames. To determine motion of the identified first boundary, the motion deriver is further configured to: determine a first region covering the first boundary at operation 412; and determine motion of the first region as motion of the first boundary. Alternatively or additionally, to determine motion of the identified first boundary, the motion deriver is further configured to: determine a second region containing only background soft tissue which is closer to the probe than the first boundary at operation 414; and determine the relative motion between the first and the second region as the motion of the first boundary at operation 416 for example in the motion detector 304, detecting, in the one filtered correlation map, a second boundary at which a value change along a direction orthogonal to the range direction of the probe exceeds a fourth predetermined threshold at operation 420 for example in the lung point detector 305, and determining a lung point based on the second boundary if the second boundary is identified.

In another example embodiment, the method further comprises deriving more than one correlation maps, each being derived from a pair of frames of a sequence of ultrasound data, each pair having a first time interval (which could be the same or varied among pairs) between the temporal frames of the pair, and a second time interval (which could be the same or varied among pairs) with respect to an adjacent pair at operation 404, filtering the more than one correlation maps to obtain one or more than one filtered correlation maps at operation 406, identifying, in the one filtered correlation map or a compounded version of the more than one filtered correlation maps, a first boundary at which a value change along a range direction of the probe exceeds a first predetermined threshold at operation 408 and 410 all together for example in the boundary identifier 303, determining motion of the identified first boundary, based on a normalized correlation function of a sequence of temporal frames. To determine motion of the identified first boundary, the motion deriver is further configured to: determine a first region covering the first boundary at operation 412; and determine motion of the first region as motion of the first boundary. Alternatively or additionally, to determine motion of the identified first boundary, the motion deriver is further configured to: determine a second region containing only background soft tissue which is closer to the probe than the first boundary at operation 414; and determine the relative motion between the first and the second region as the motion of the first boundary at operation 416 for example in the motion detector 304, detecting, in a compounded version of the more than one filtered correlation map, a second boundary at which a value change along a direction orthogonal to the range direction of the probe exceeds a fourth predetermined threshold at operation 420 for example in the lung point detector 305, and determining a lung point, based on the second boundary if the second boundary is identified.

It is advantageous to have a compounded version of ultrasound data maps or correlation maps for analyzing, because the compounded version could have a better signal-to-noise ratio (SNR), better detectability for the first boundary and could reduce artifacts (for example, caused by small hand motion).

The method further comprises displaying the identification of the first boundary, the determined motion of the first boundary, the identification of the second boundary, and/or the determination of lung point existence, via a user interface, which can be, for example, a display.

The method may further comprise determining the size of the PTX, for example in the form of volume of the pneumothorax, estimated by means of the contour of the pneumothorax outlined by ascertaining lung points at different intercostal spaces and lining up those lung points at operation 424, determining the size of the lung, in the form of volume of a cavity formed in the pleural interface at operation 426 and determining the percentage of the pneumothorax defined as the ratio between the volume of the pneumothorax and that of the lung at operation 428, operations 424, 426 and 428 for example all performed in the PTX quantifier 307. In practice, the length of one side of the chest wall could be estimated according to the figure of the patient, and as the chest wall or lung shape is a certainty factor (Each lung is somewhat triangular in shape with the apex being superior and the base being inferior), the percentage of the pneumothorax defined as the size of the PTX over the length of one side of the chest wall along one direction could be estimated. In this way, the pneumothorax could be quantified, automatically. The quantification results can be presented to a user via a user interface.

In some example embodiments, it should also be appreciated that the ultrasound data map could be a short time energy (STE) map. As a STE map is obtained once the amplitude is obtained and involves no quantization and coding, it is more computation efficient.

The STE maps could be generated from any of video image data (i.e., Digital Imaging and Communications in Medicine (DICOM) data), channel un-beamformed radio frequency (RF) data (i.e., channel data), and beamformed RF data (i.e., radio frequency data) obtained or processed after being obtained by the probe 10.

In an example embodiment, a pulse inversion (PI) version of ultrasound RF signals in the tissue harmonic imaging mode is selected as the temporal frames for analysis and processing.

It should be understood by one skilled in the art that radio frequency data in the fundamental imaging mode may also be selected for analysis and processing.

It should also be appreciated that the correlation can be determined from temporal frames that are signals processed from received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from the body.

As is described above, when determining the motion of the identified first boundary, based on a normalized correlation function of the sequence of the temporal frames, filtering is not required. However, when the pleural line is determined by a person skilled in the art, filtering is normally required to meet accuracy requirements; otherwise, the detection based on this analyzing result will not be accurate, resulting in a fatal threat to the patients.

Figure 5:
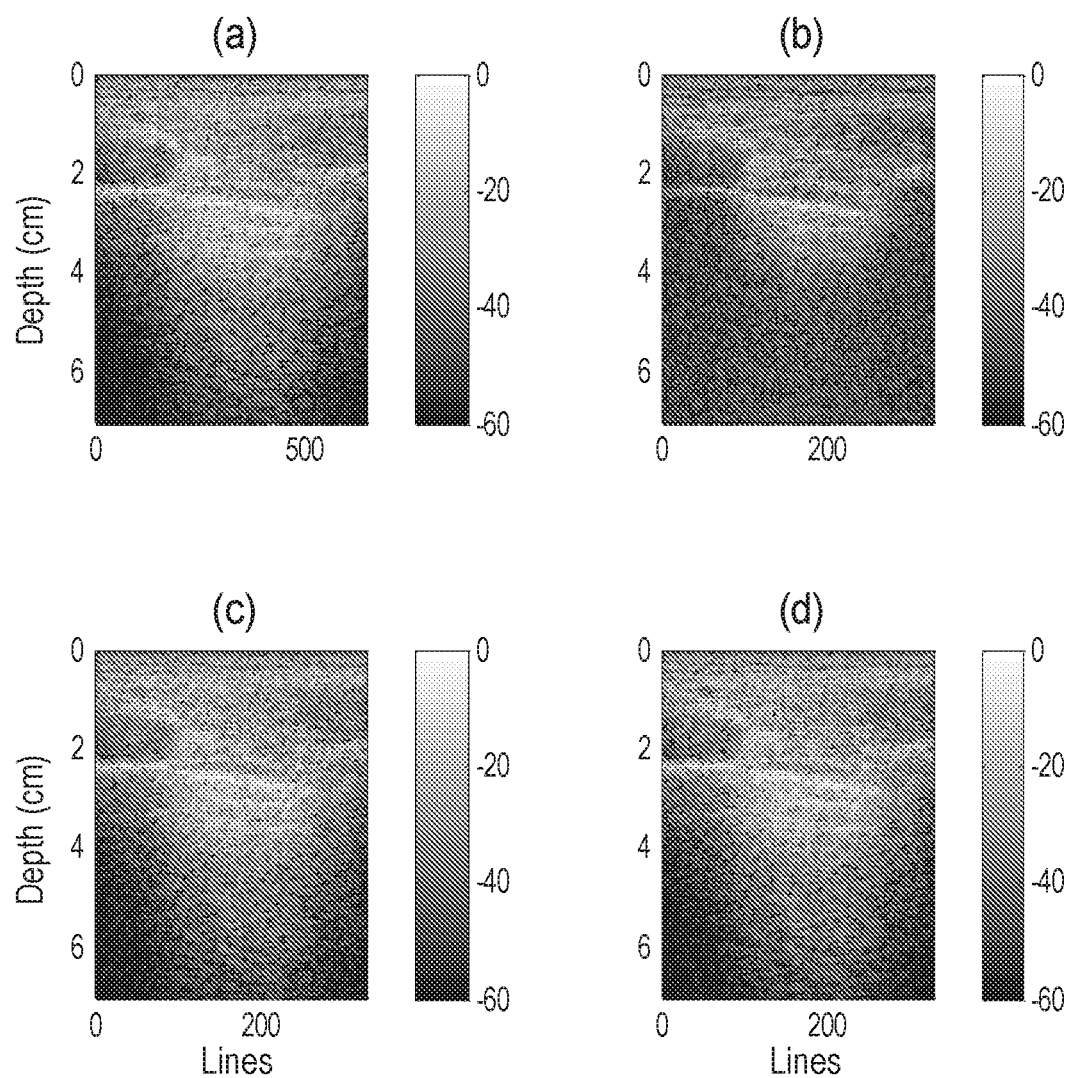
FIG. 5 illustrates data collected in the tissue harmonic imaging mode from a healthy subject.

FIG. 5 illustrates data collected in the tissue harmonic imaging mode from a healthy subject, for example, a B-scan image from RF data (640 lines as original version) shown in FIG. 5(*a*), a pulse inversion (320 lines as PI version) shown in FIG. 5(*b*), a positive transmission version (320 lines called positive version) shown in FIG. 5(*c*) and a negative transmission version (320 lines called negative version) shown in FIG. 5(*d*). It is noted that the PI version shown in FIG. 5(*b*) has the highest resolution for identifying the first boundary between two ribs at both sides.

In an example embodiment, the correlation map is a temporal correlation coefficient (CC) map; alternatively, the correlation map is a normalized correlation coefficient (NCC) map. The correlation coefficient is also referred to as Pearson product-moment correlation coefficient (PPMCC), developed by Karl Pearson from a related idea introduced by Francis Galton in the 1880s.

Both the CC map and the NCC map are effective in motion identification, but the CC map requires less computation than the NCC map. However, for an ultrasound imaging system already implementing the NCC solution, the NCC map could be applied directly, thus the computation complexity of the data analyzer 20 could be reduced. Besides, the NCC map could make up for the varied brightness of different frames.

In an example embodiment, a sliding window with a window size of 5-60 samples is applied in deriving the ultrasound data maps or the correlation map(s), preferably a window size of 25-35 samples is applied, for example, 30 samples. A short sliding window should be used to have a high resolution to identify small differences between 2 frames, but a short sliding window results in a large variance in correlation coefficient. In order to determine the optimal window size, we change the window size from 5 samples to 60 at increments of 5 samples. As the window size changes from 5 samples to 60 samples, it is noted that a long window size results in huge computations but does not lead to a substantial increase in performance, and the variability of the ultrasound data map becomes less when the window size is between 25 samples and 35 samples. There is a similar trend for correlation maps as for ultrasound data maps. Therefore, it is a compromise that a window size of 30 samples is selected for data analysis and, at a later point in time, processing, which is a balance between computation load and performance.

Figure 6:
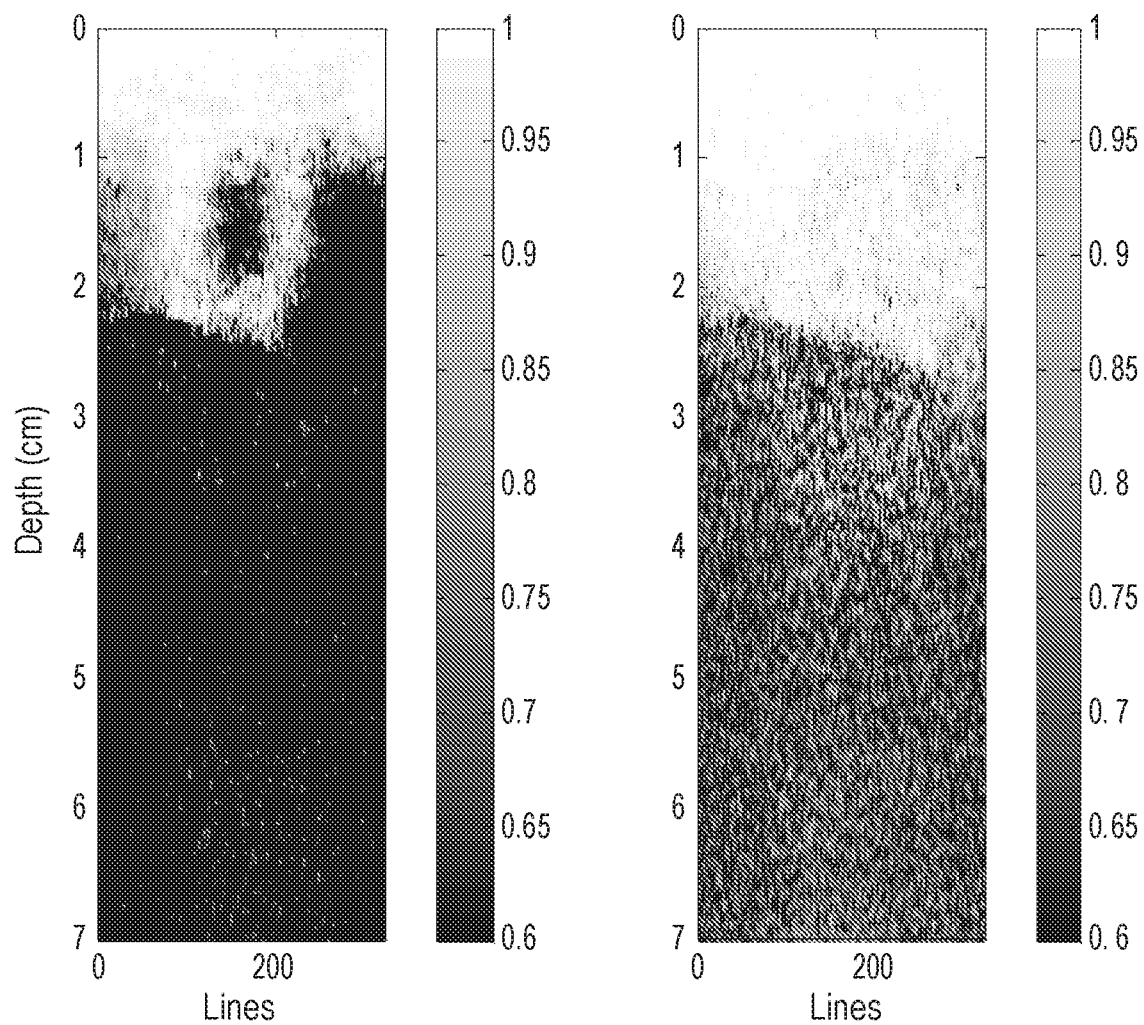
FIG. 6 illustrates two correlation maps based on radio frequency data and radio frequency amplitude data respectively.

In an example embodiment, the correlation map is built using amplitude data extracted from ultrasound radio frequency data. FIG. 6 illustrates an RF data based temporal correlation coefficient map (left) and an RF amplitude data based temporal correlation coefficients map (right) with the window size of 30 samples over two temporal frames. Compared with correlation map(s) from ultrasound RF data, correlation map(s) from amplitude data extracted from ultrasound RF data show(s) very robust results in identifying the first boundary (as described in the summary) and its upper area where there is less motion between two sequential frames (and thus more coherence between two sequential frames), and also in identifying a lower area below the boundary line where more random RF data is presented (and thus less coherence between two sequential frames). The reason for the differences between the two shown temporal correlation coefficient maps may be due to a phase sensitive issue in RF data, wherein artifacts are caused either by the ultrasound transducer in the probe not keeping still during data collection or out of plane motion due to breathing.

In an example embodiment of operation 404, the ultrasound data maps and correlation maps are built using amplitude data extracted from ultrasound data, which has an advantage over those built using ultrasound data directly, for similar reasons as described above.

It should be appreciated by a person skilled in the art that the ultrasound data maps and correlation maps can be built from temporal frames that are signals processed from received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from the body.

In an example embodiment of operation 406, after obtaining the correlation map(s) and ultrasound data maps, a 2D median filter is applied to said two kinds of maps, to reduce noises, followed by the application of a 2D Gaussian filter for further smoothing.

FIG. 7a through FIG. 7h combine to form a complete FIG. 7 view, where the sub-view is referenced within brackets. illustrates identification of the first boundary of one example embodiment shown in maps. Those maps are obtained by placing the probe on the body surface across two ribs, wherein the long side of the probe is perpendicular to the ribs. FIG. 7 shows an original CC map (a), a filtered CC map after 2D median filtering and then 2D Gaussian filtering (b), profiles, namely the values along the 200th scanning line for the original CC map (shown in a dotted line) and the filtered CC map (shown in a solid line) (c), identified first boundary (shown in a white curve) overlaid on the original CC map (d), an original STE map (e), 2D median filtered version of the original STE map (f), 2D Gaussian filtered version of the 2D median filtered version of the original STE map overlaid with detected solid line (shown in a bright line) (g), and final identified first boundary (shown in a white line between two ribs) overlaid on an original pulse-inversion ultrasound image (h).

Figure 7A:
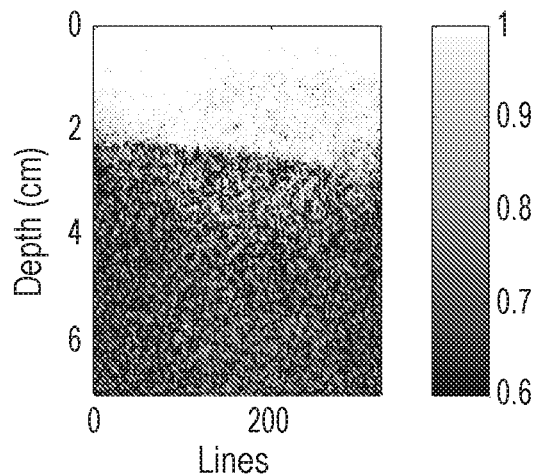
FIG. 7a, FIG. 7b, FIG. 7c, FIG. 7d, FIG. 7e, FIG. 7f, FIG. 7g and FIG. 7h combine to form a complete FIG. 7 view, which illustrates first boundary detection of one example embodiment shown in maps.
Figure 7B:
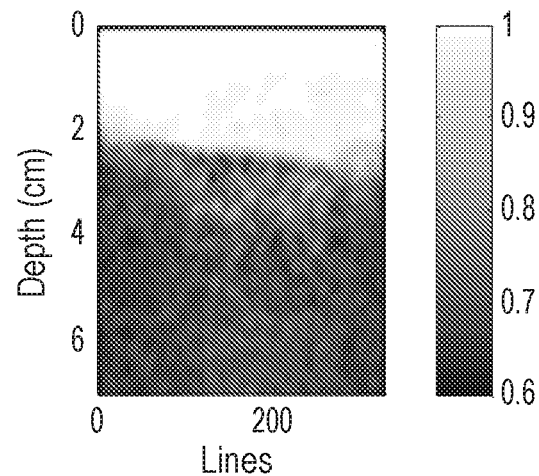
Figure 7C:
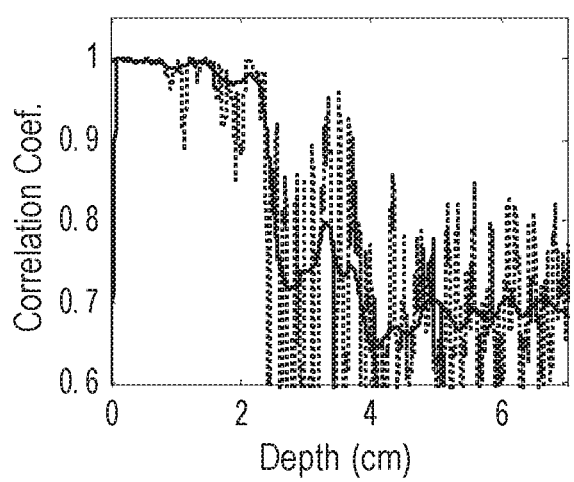
Figure 7D:
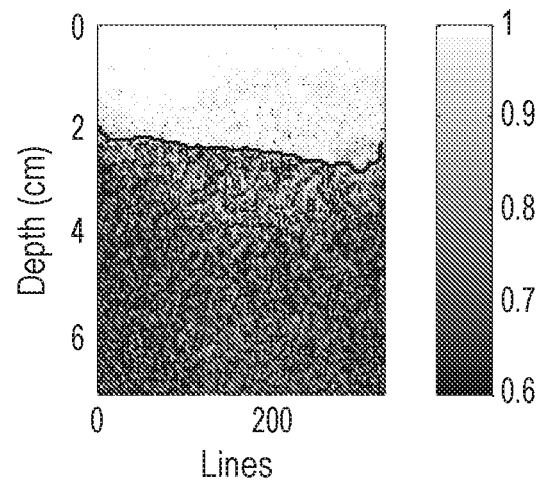
Figure 7E:
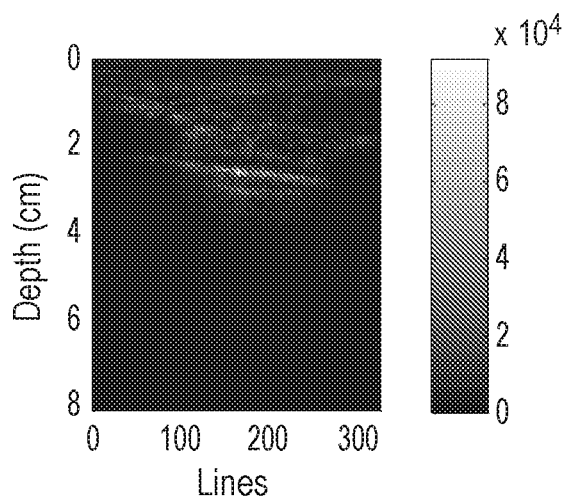
Figure 7F:
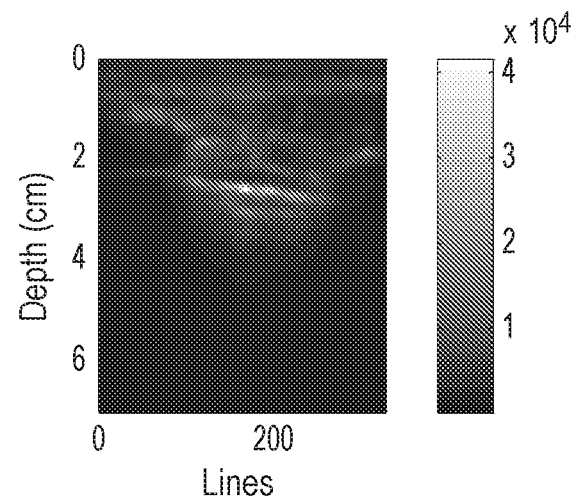
Figure 7G:
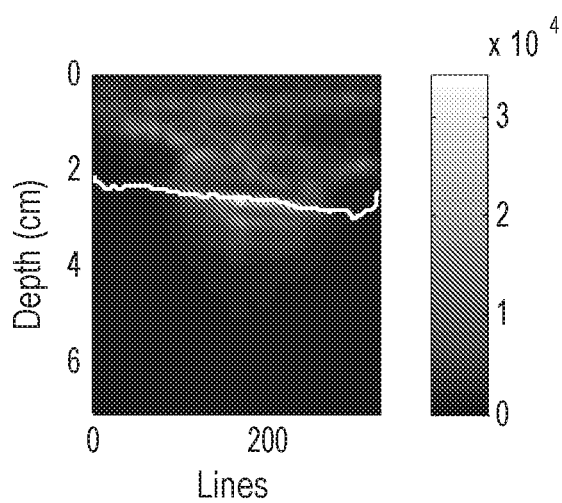
Figure 7H:
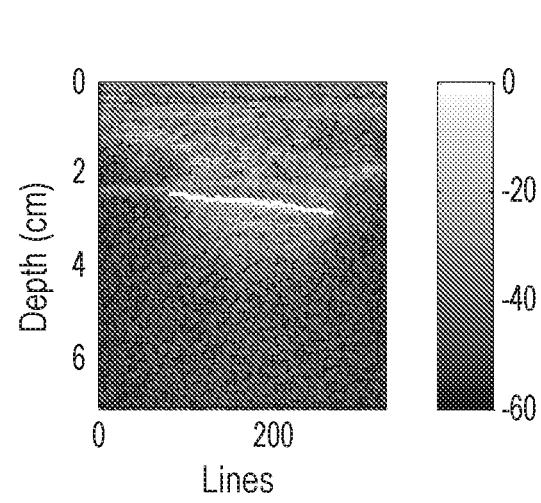

FIGS. 7(a), (e) and (f) result from operation 404. FIG. 7(b) results from operation 406. FIG. 5(c) shows that the filtered version is smoother. FIG. 7(d) results from operation 408. FIG. 7(g) results from a combination of operations 406 and 408. FIG. 7(h) results from combination of operations 402 and 410.

In an example embodiment of operation 408, for each line of a plurality of scanning lines (the scanning line, as is known in the art, is along the extension of the ultrasound wave, also called receiving line), a point where there is a sharp value change on the scanning line which exceeds a first predetermined threshold in the one filtered correlation map or the compounded version of the more than one filtered correlation map is identified, and then all such identified points along the plurality of scanning lines form the first boundary line. For example, the value change can be determined based on a value slope of a point along the scanning line in the filtered correlation map, or based on the simple fact that the value drops from approximately 1 to 0.8 along the scanning line in the filtered normalized correlation coefficient map.

In an example embodiment, operation 404 further comprises deriving one or more ultrasound data maps, each ultrasound data map being derived from a corresponding one of a plurality of frames of the ultrasound data in temporal order, and at operation 410, a start point and an end point on the first boundary is identified by comparing the one filtered ultrasound data map or the compounded version of the more than one filtered ultrasound data maps with a second and a third predetermined threshold, wherein the starting point is identified as a point on the first boundary at which there is a sharp value increase (for example: with maximum slope) in the one filtered ultrasound data map or the compounded version of the more than one filtered ultrasound data maps, which exceeds a second predetermined threshold, and the end point is detected as a point on the first boundary at which there is a sharp value decrease (for example: with minimum slope) in one of the two filtered ultrasound data maps or the compounded version of the more than one filtered ultrasound data maps, which exceeds a third predetermined threshold.

In an example embodiment, absolute values of the maximum slope and the minimum slope are the same, therefore the second predetermined threshold equals the third predetermined threshold.

In an example embodiment, absolute values of the maximum slope and the minimum slope are not the same, therefore the second predetermined threshold does not equal the third predetermined threshold.

In an example embodiment, any of the predetermined thresholds could be determined from experiences or statistical values.

In an example embodiment of operation 416, the determined motion could be displacements and/or velocities in vertical direction or horizontal direction or both.

As is known in the art, the direction along the scanning line is the vertical direction (also called the range direction of the probe), and any direction in the plane orthogonal to the vertical direction, e.g. azimuth direction or elevation direction, is the horizontal direction.

Figure 8:
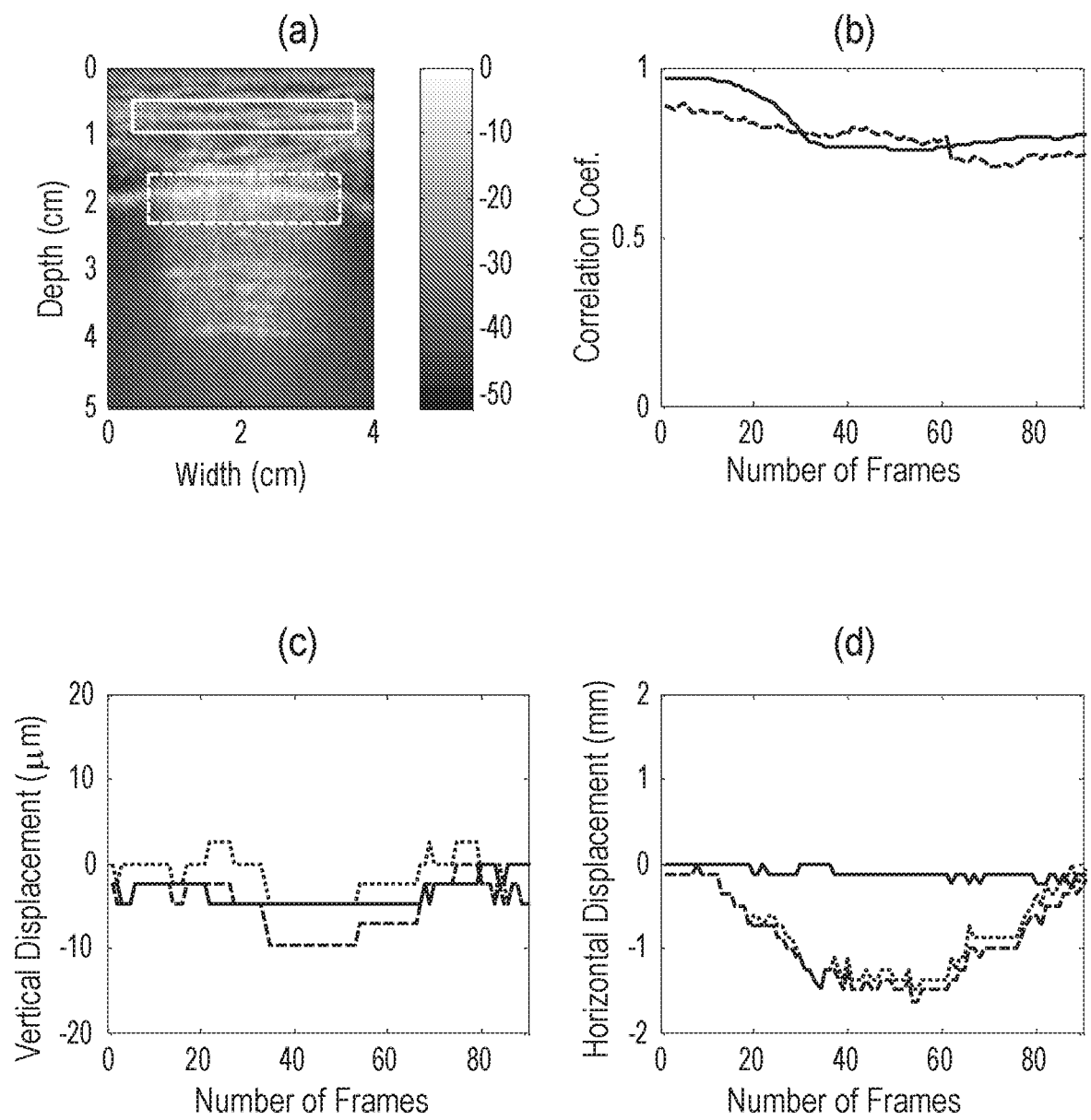
FIG. 8 illustrates motion detection of the first boundary of one example embodiment shown in maps.
Figure 9:
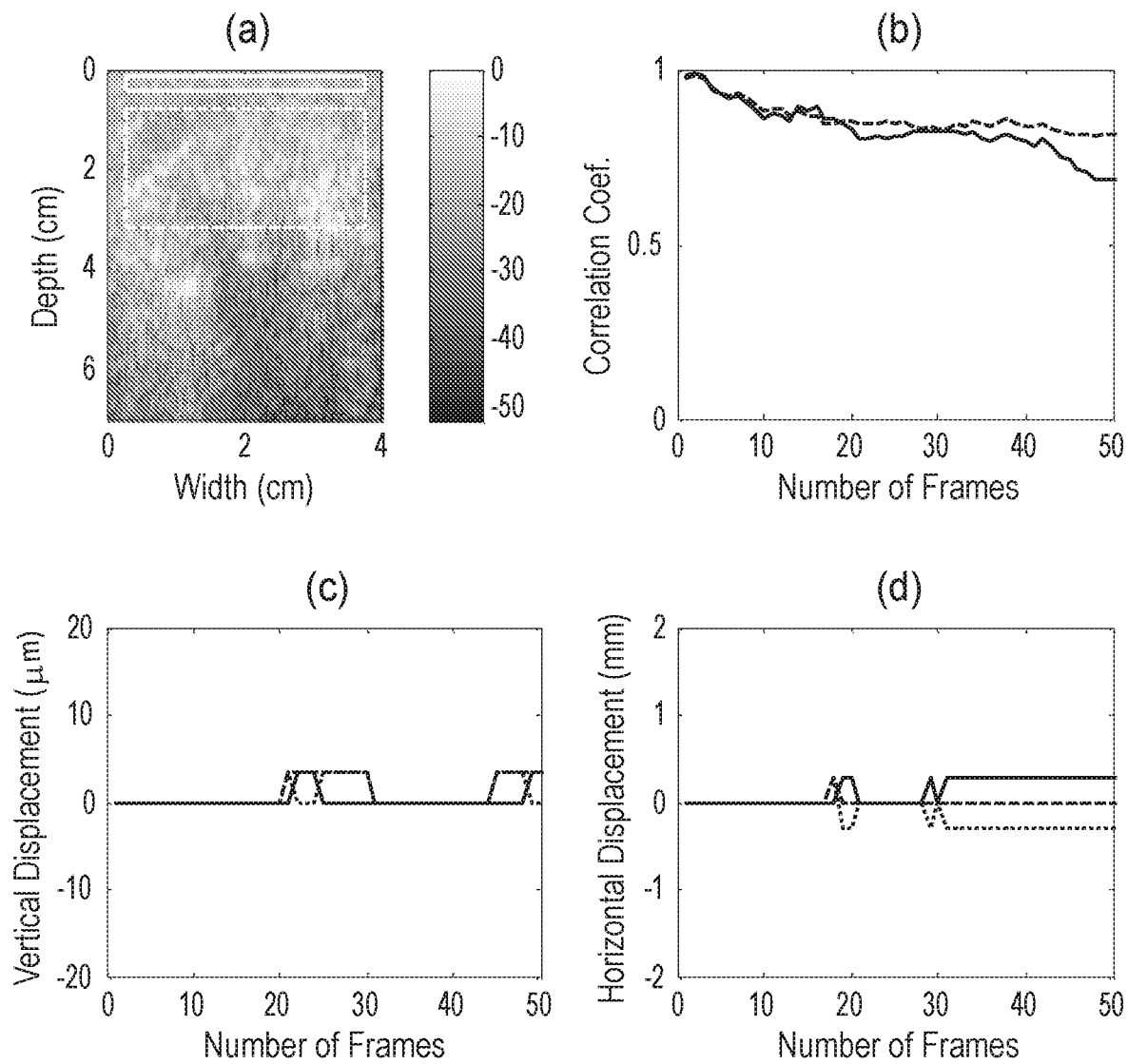
FIG. 9 illustrates motion detection of pneumothorax of one example embodiment shown in maps.

In an example embodiment of operation 422, more than average motion in the horizontal direction is determined in a subject as shown in FIG. 8, and on the other hand, less than average motion in the horizontal direction is determined as PTX cases as shown in FIG. 9.

FIG. 8 illustrates motion detection of the first boundary of one example embodiment shown in maps, wherein the lower box (in dashed line) indicates the area within which the first boundary is situated, with the width of the first region covering the whole first boundary, and the upper box (in solid line) is for indicating background soft tissue at a shallower depth, i.e., above the boundary line (a), corresponding correlation coefficients (shown in a dashed line for the first boundary and a solid line for background soft tissue) changing with the number of frames (b), corresponding displacements in vertical direction (shown in a dashed line for the first boundary, a solid line for indicating background soft tissue and relative displacement between two lines marked in a dotted line) (c), corresponding displacements in horizontal direction (shown in a dashed line for the first boundary, a solid line for background soft tissue and relative displacement between two lines is marked in a dotted line) (d).

FIG. 9 illustrates motion detection of a pneumothorax of one example embodiment shown in maps, wherein the lower box (in dashed line) indicates the area within which the gas pocket is situated and the upper box (in solid line) is for indicating background soft tissue at a shallower depth, i.e., above the gas pocket (a), corresponding correlation coefficients (shown in a dashed line for gas pocket and a solid line for background soft tissue) changing with number of frames (b), corresponding displacements in vertical direction (shown in a dashed line for gas pocket area, a solid line for background soft tissue and relative displacement between two lines is marked in a dotted line) (c), and corresponding displacements in horizontal direction (shown in a dashed line for gas pocket, a solid line for background soft tissue and relative displacement between two lines is marked in a dotted line) (d).

Delineation of the lower box is as follows: as the first boundary moves due to lung sliding, no part of the first boundary will move out of the box. Therefore, a redundancy of 20% to 30% is reserved with respect to width and length of the box as compared to the size of the first boundary. A motion of the first boundary between two frames can be determined from the lower box only, as in most cases the patient to be scanned lies down and keeps still. Considering flexibility, a relative motion between the upper box and lower box is applied to determine motion of the first boundary between two frames. For example, suppose the horizontal position of a point in the upper box in the first frame is $P_{u1}$, the horizontal position of the point in the upper box in the second frame is $P_{u2}$, the horizontal position of another point in the lower box in the first frame is $P_{L1}$, the horizontal position of said another point in the lower box in the second frame is $P_{L2}$, then in a first embodiment, horizontal displacement of said another point between the first frame and the second frame is $\Delta P$, $\Delta P = P_{L2} - P_{L1}$. Horizontal displacement of every point in the box can be calculated in this way; an average displacement of all the points in the box could be obtained, and the average displacement is taken as the displacement of the first boundary, which indicates at least part of the pleural interface of the subject. In a second embodiment, horizontal displacement of said another point between the first frame and the second frame is $\Delta P$, $\Delta P = (P_{L2} - P_{L1}) - (P_{u2} - P_{u1})$. Similarly, an average displacement of all the points in the lower box subtracted from an average displacement of all the points in the upper box is taken as the displacement of at least part of a pleural interface. Furthermore, as the frame rate is known, the time interval $\Delta T$ between the first frame and the second frame is consequently also known, and the horizontal velocity of the point can also be calculated as: $V = \Delta P / \Delta T$. Vertical displacement and velocity of the first boundary can be calculated in a similar way. It will be appreciated by one skilled in the art that such displacement and velocity parameters are crucial in PTX detection and no prior art can provide them directly and automatically.

It is concluded from FIG. 8 and FIG. 9 that more motion in horizontal direction is found for a normal healthy subject and less motion in horizontal direction, compared to that of a normal healthy subject, is found for a pneumothorax case.

The averaged velocity (AV) computed could be used in another way to determine lung sliding. If the averaged velocity computed from FIG. 8 or 9 exceeds a velocity threshold, there is deemed to be lung sliding. Otherwise, there is deemed to be no lung sliding.

Actually, motion in the vertical direction of FIG. 8 and FIG. 9 could also be compared to determine a normal healthy subject or a pneumothorax case. However, as can be seen from FIG. 8 and FIG. 9, a normal lung has less motion in the vertical direction than in the horizontal direction due to lung sliding mostly in the horizontal direction, so comparison in the horizontal direction could improve the accuracy of determination.

Figure 10:
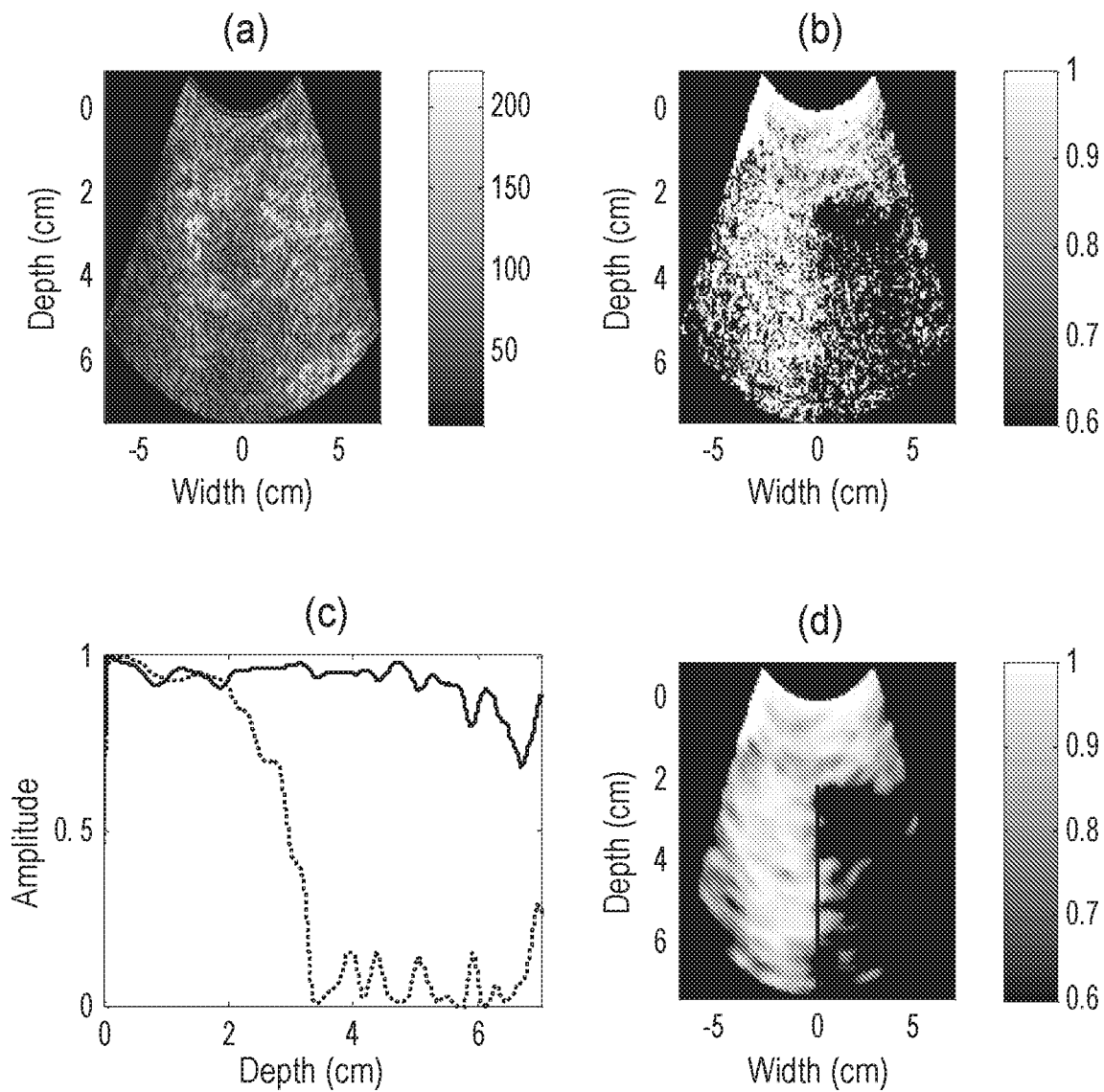
FIG. 10 illustrates lung point detection of one example embodiment shown in maps.

In an example embodiment of operation 422, if a lung point is detected, a pneumothorax is determined to be present in the pleural interface. The lung point is found as a point on the surface of the scanned subject where there is a pattern change between an area with all high normalized correlation coefficients for the pneumothorax and an area with both low correlation coefficients and high correlation coefficients (compared with the high correlation coefficients) in the one filtered correlation map or the compounded version of the more than one filtered correlation map. FIG. 10 illustrates lung point detection of one example embodiment, shown in maps, wherein it shows a B-scan image (a), its corresponding correlation coefficient map (b), the smoothed correlation coefficient map (d), and profiles (c) at −3 cm showing where a pneumothorax is present (the dotted line) as well as at +3 cm showing an area of a normal lung part (the solid line). It can be seen that the lung point (shown in the light line almost in the middle of the ultrasound image) is between the pneumothorax and a normal lung part in (d). As shown in FIG. 10 (d), after the second boundary is identified, a curve fitting line generated from those points is formed, and the intersection point of this line and the surface of the imaged subject is the lung point.

In an example embodiment, operation 402 is performed by the probe 10, and operations 404 to 428 are performed by the data analyzer 20.

While the embodiments have been illustrated and described herein, it will be understood by those skilled in the art that various changes and modifications may be made, and equivalents may be substituted for elements thereof without departing from the true scope of the present technology. In addition, many modifications may be made to adapt to a particular situation and the teaching herein without departing from the central scope. Therefore, it is intended that the present embodiments not be limited to the particular embodiments disclosed as the best mode contemplated for carrying out the present technology, but that the present embodiments include all embodiments falling within the scope of the appended claims.

The invention claimed is:

1. An ultrasound system for scanning a lung of a subject comprising:
   a probe configured to obtain a sequence of temporal frames of ultrasound data relating to a scanning region including at least part of a pleural interface of the lung, each temporal frame of ultrasound data at least extending along a range direction of the probe; and
   a data analyzer, comprising a processing circuitry, and configured to:
      derive one or more than one correlation maps, each correlation maps being derived from a pair of temporal frames of the sequence of temporal frames;
      filter the one or more than one correlation maps to obtain one or more than one filtered correlation maps;
      derive one or more than one ultrasound data maps, each ultrasound map being derived from one temporal frame or a compounded version of more than one temporal frames of the sequence of temporal frames;
      filter the one or more than one ultrasound data maps to obtain one or more than one filtered ultrasound data maps;
      identify a first boundary line comprising a point from each line of a plurality of scanning lines, at which point a value change along the scanning line exceeds a first predetermined threshold in the one filtered correlation map or a compounded version of the more than one filtered correlation maps;
      identify a starting point as a point at which there is a value increase along the first boundary line in the one filtered ultrasound data map or the compounded version of the more than one filtered ultrasound data maps, which value increase exceeds a second predetermined threshold;
      identify an end point as a point at which there is a value decrease along the first boundary line in the one filtered ultrasound data map or the compounded version of the more than one filtered ultrasound data maps, which value decrease exceeds a third predetermined threshold.

2. The system of claim 1, wherein deriving one or more than one correlation maps comprises deriving one or more than one cross correlation maps.

3. The system of claim 1, wherein the data analyzer is further configured to:
   determine motion of the identified first boundary, based on a normalized correlation function of the sequence of the temporal frames.

4. The system of claim 1, wherein the data analyzer is further configured to:
   determine motion of the identified first boundary, based on a normalized cross correlation function of the sequence of the temporal frames.

5. The system of claim 4, wherein to determine motion of the identified first boundary, the data analyzer is further configured to:
   determine a first region covering the first boundary; and
   determine motion of the first region as motion of the identified first boundary.

6. The system of claim 5, wherein, to determine motion of the identified first boundary, the data analyzer is further configured to:
   determine a second region containing only background soft tissue which is closer to the probe than the first boundary; and
   determine the relative motion between the first and the second region as the motion of the identified first boundary.

7. The system of claim 1, wherein the data analyzer is further configured to:
   identify, in the one filtered correlation map or a compounded version of the more than one filtered correlation maps, a second boundary at which a value change in coefficients of the corresponding map along a direction orthogonal to the range direction exceeds a fourth predetermined threshold.

8. The system of claim 7, wherein the data analyzer is further configured to determine a lung point, based on the second boundary if the second boundary is identified.

9. The system of claim 1, further comprising a display, configured to present the ultrasound data and processed data.

10. A method of scanning a lung of a subject using ultrasound, comprising:
   obtaining a sequence of temporal frames of ultrasound data relating to a scanning region including at least part of a pleural interface of the lung, each temporal frame of ultrasound data at least extending along a range direction of the probe;
   deriving one or more than one correlation maps, each from a pair of temporal frames of the sequence of temporal frames;
   filtering the one or more than one correlation maps to obtain one or more than one filtered correlation maps;
   deriving one or more than one ultrasound data maps, each ultrasound map being derived from one temporal frame or a compounded version of more than one temporal frames of the sequence of temporal frames;
   filtering the one or more than one ultrasound data maps to obtain one or more than one filtered ultrasound data maps;
   identifying a first boundary line comprising a point from each line of a plurality of scanning lines, at which point a value change along the scanning line exceeds a first predetermined threshold in the one filtered correlation map or a compounded version of the more than one filtered correlation maps;
   identify a starting point as a point at which there is a value increase along the first boundary line in the one filtered ultrasound data map or the compounded version of the more than one filtered ultrasound data maps, which value increase exceeds a second predetermined threshold; and identifying an end point as a point at which there is a value decrease along the first boundary line in the one filtered ultrasound data map or the compounded version of the more than one filtered ultrasound data maps, which value decrease exceeds a third predetermined threshold.

11. The method of claim 10, further comprising:
determining motion of the identified first boundary, based on a normalized correlation function derived from the sequence of the temporal frames.

12. The method of claim 11, wherein determining motion of the identified first boundary comprises:
determining a first region covering the first boundary; and
determining motion of the first region as the motion of the first boundary.

13. The method of claim 12, wherein determining motion of the identified first boundary comprises:
determining a second region only containing background soft tissue which is closer to the probe than the first boundary;
determining the relative motion between the first and the second region as the motion of the first boundary.

14. The method of claim 13, further comprising:
detecting, in the one filtered correlation map or a compounded version of the more than one filtered correlation maps, a second boundary at which a value change along a direction orthogonal to the range direction exceeds a fourth predetermined threshold.

15. An ultrasound system for scanning a lung of a subject, comprising:
a probe configured to obtain a sequence of temporal frames of ultrasound data relating to a region including at least part of a pleural interface of the lung, each temporal frame of ultrasound data at least extending along a range direction of the probe; and
a data analyzer, comprising:
a map deriver configured to derive one or more than one correlation maps, each correlation map being derived from a pair of temporal frames of the sequence of temporal frames, and to derive one or more than one ultrasound data maps, each ultrasound map being derived from one temporal frame or a compounded version of more than one temporal frames of the sequence of temporal frames;
a map filter configured to filter the one or more than one correlation maps to obtain one or more than one filtered correlation maps, and to filter the one or more than one ultrasound data maps to obtain one or more than one filtered ultrasound data maps;
a boundary identifier configured to identify a first boundary line comprising a point from each line of a plurality of scanning lines, at which point a value change along the scanning line exceeds a first predetermined threshold in the one filtered correlation map or a compounded version of the more than one filtered correlation maps, to identify a starting point as a point at which there is a value increase along the first boundary line in the one filtered ultrasound data map or the compounded version of the more than one filtered ultrasound data maps, which value increase exceeds a second predetermined threshold, and to identify an end point as a point at which there is a value decrease along the first boundary line in the one filtered ultrasound data map or the compounded version of the more than one filtered ultrasound data maps, which value decrease exceeds a third predetermined threshold.

* * * * *